(12) United States Patent
Nitta

(10) Patent No.: US 8,146,590 B2
(45) Date of Patent: Apr. 3, 2012

(54) HUMIDIFICATION SYSTEM FOR BREATHING CIRCUIT

(75) Inventor: Kazufuku Nitta, Kawaguchi (JP)

(73) Assignee: METRAN Co., Ltd., Kawaguchi-shi, Saitama (JP)

( * ) Notice: Subject to any disclaimer, the term of this patent is extended or adjusted under 35 U.S.C. 154(b) by 792 days.

(21) Appl. No.: 11/816,381

(22) PCT Filed: Feb. 14, 2006

(86) PCT No.: PCT/JP2006/302499
§ 371 (c)(1),
(2), (4) Date: Dec. 1, 2008

(87) PCT Pub. No.: WO2006/088006
PCT Pub. Date: Aug. 24, 2006

(65) Prior Publication Data
US 2009/0126735 A1    May 21, 2009

(30) Foreign Application Priority Data

Feb. 15, 2005    (JP) .................................. 2005-037408

(51) Int. Cl.
*A62B 18/08*    (2006.01)
(52) U.S. Cl. ............................... 128/203.26; 128/205.12
(58) Field of Classification Search ............. 128/203.26, 128/205.12, 201.13
See application file for complete search history.

(56) References Cited

U.S. PATENT DOCUMENTS

| | | | | |
|---|---|---|---|---|
| 3,695,267 A | * | 10/1972 | Hirtz et al. ............... | 128/203.17 |
| 4,010,748 A | * | 3/1977 | Dobritz .................... | 128/203.27 |
| 4,086,305 A | * | 4/1978 | Dobritz ........................... | 261/30 |
| 4,248,217 A | * | 2/1981 | Brisson .................... | 128/204.17 |
| 4,327,717 A | * | 5/1982 | Oetjen et al. ............. | 128/201.13 |
| 4,355,636 A | * | 10/1982 | Oetjen et al. ............. | 128/204.13 |
| 4,367,734 A | * | 1/1983 | Benthin ..................... | 128/204.13 |
| 4,369,777 A | * | 1/1983 | Lwoff et al. ............. | 128/200.16 |
| 4,381,267 A | * | 4/1983 | Jackson ....................... | 261/104 |
| 4,430,994 A | * | 2/1984 | Clawson et al. ......... | 128/203.27 |
| 4,436,674 A | * | 3/1984 | McMenamin .............. | 261/64.3 |
| 4,674,494 A | * | 6/1987 | Wiencek .................. | 128/203.16 |
| 4,676,237 A | * | 6/1987 | Wood et al. ............. | 128/203.17 |
| 4,708,831 A | * | 11/1987 | Elsworth et al. ............. | 261/130 |
| 4,753,758 A | * | 6/1988 | Miller .......................... | 261/139 |
| 4,770,168 A | * | 9/1988 | Rusz et al. ............... | 128/203.12 |
| 4,771,770 A | * | 9/1988 | Artemenko et al. ...... | 128/201.13 |
| 4,829,998 A | * | 5/1989 | Jackson ................... | 128/203.12 |
| 5,172,686 A | * | 12/1992 | Anthony .................. | 128/203.16 |

(Continued)

FOREIGN PATENT DOCUMENTS

DE        3617031 A1    12/1986

(Continued)

*Primary Examiner* — Stephen Crow
(74) *Attorney, Agent, or Firm* — Christensen, O'Connor, Johnson, Kindness, PLLC

(57) ABSTRACT

There is provided a humidification system for a breathing circuit that can detect abnormality in flow of intake air inside an inspiration tube. A humidification section is arranged inside an inspiration tube of a breathing circuit. Further, the humidification system is constructed capable of supplying moisture into intake air flowing inside the inspiration tube by using, for example, hydrophobic hollow fibers or a hydrophobic membrane. The flow section comprises a supply section for supplying moisture to the humidification section and a delivery section for delivering moisture that has been supplied to the humidification section. The control section detects intake air abnormality using difference information for water temperature of the supply section and water temperature of the delivery section.

12 Claims, 1 Drawing Sheet

U.S. PATENT DOCUMENTS

| | | | | |
|---|---|---|---|---|
| 5,226,411 | A * | 7/1993 | Levine | 128/203.26 |
| 5,367,604 | A * | 11/1994 | Murray | 392/394 |
| 5,392,770 | A * | 2/1995 | Clawson et al. | 128/203.27 |
| 5,435,298 | A * | 7/1995 | Anthony | 128/201.13 |
| 5,537,996 | A * | 7/1996 | McPhee | 128/204.17 |
| 5,640,951 | A * | 6/1997 | Huddart et al. | 128/204.17 |
| 6,394,084 | B1 | 5/2002 | Nitta | |
| 6,755,399 | B2 * | 6/2004 | Shimanuki et al. | 261/104 |
| 7,111,624 | B2 * | 9/2006 | Thudor et al. | 128/203.16 |
| 7,588,029 | B2 * | 9/2009 | Smith et al. | 128/203.17 |
| 7,616,871 | B2 * | 11/2009 | Kramer | 392/403 |
| 7,647,925 | B2 * | 1/2010 | Mantell et al. | 128/204.17 |
| 7,762,251 | B2 * | 7/2010 | Mantell et al. | 128/204.17 |

FOREIGN PATENT DOCUMENTS

| | | |
|---|---|---|
| GB | 1520836 A | 8/1978 |
| JP | 55-38190 | 3/1980 |
| JP | 04-121540 | 4/1992 |
| JP | 9-122242 A | 5/1997 |

* cited by examiner

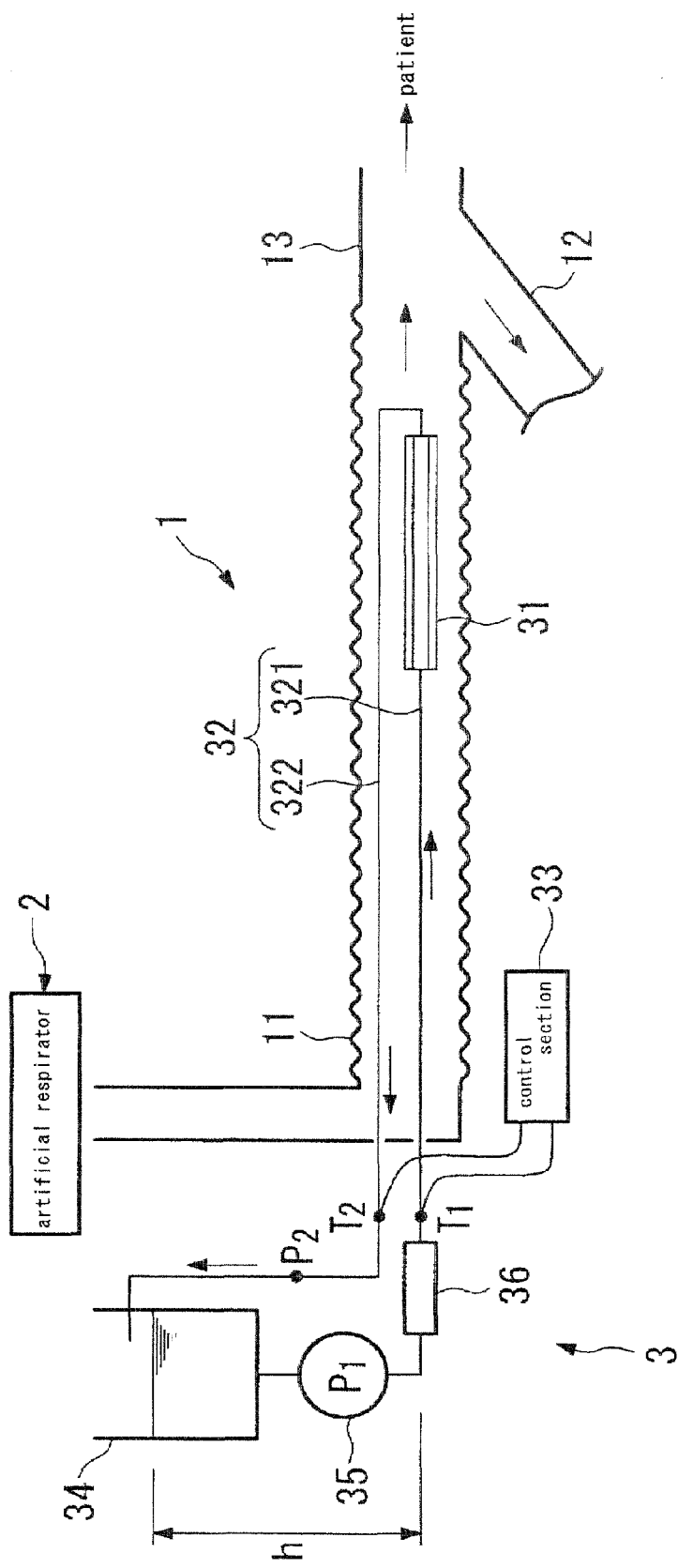

HUMIDIFICATION SYSTEM FOR BREATHING CIRCUIT

BACKGROUND

1. Field of the Invention

The present invention relates to a humidification system for a breathing circuit.

2. Description of the Related Art

Conventionally, breathing circuits for artificial respiration are used. An artificial respirator is connected to the beginning of an inspiration tube of a breathing circuit, and it is possible to supply intake air to a patient.

In breathing circuits, there is a danger of supply of intake air being interrupted, for whatever cause, such as failure of the artificial respirator, damage to the breathing circuit, etc. It is therefore necessary for the fact that intake air is being supplied correctly to be monitored by some means.

On the other hand, the present applicants have proposed an apparatus that performs humidification of intake air by arranging hollow fibers inside an inspiration tube (refer to patent publication 1 below).

Patent Publication 1: Japanese patent laid-open No. Hei. 9-122242

The present invention has been conceived in view of the above-described situation and provides a humidification system for a breathing circuit that can detect abnormality in flow of intake air inside an inspiration tube.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

The humidification system for a breathing circuit of the present invention is provided with a humidifier section, a flow section, and a control section. The humidification section is arranged inside an inspiration tube of the breathing system. The humidification section is constructed to be able to supply moisture into intake air flowing inside the inspiration tube. The flow section comprises a supply section for supplying moisture to the humidification section and a delivery section for delivering moisture that has been supplied to the humidification section. The control section is configured to detect abnormality using difference information for water temperature in the supply section and water temperature in the delivery section.

It is possible to construct the humidification section using hydrophobic hollow fibers or a hydrophobic membrane.

It is possible to arrange the humidification system close to a patient side end section of the inspiration tube.

It is possible for all or part of the flow section to be arranged inside the inspiration tube.

The control section performs the abnormality detection with "difference between water temperature of supply section and water temperature of delivery section is less than or equal to a specified value" as a condition.

Pressure of the moisture delivered to the flow section and the humidification section is preferably a higher value than the internal pressure of the inspiration tube of the breathing circuit.

According to the present invention, it is possible to provide a humidification system for a breathing circuit that can detect abnormality in flow of intake air inside an inspiration tube.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 1 is an explanatory drawing showing the schematic structure of a humidification system of one embodiment of the present invention.

DETAILED DESCRIPTION

In the following, one embodiment of a humidification system for a breathing circuit of the present invention will be described with reference to the attached drawings.

Structure of this Embodiment

First of all, the structure of a breathing circuit 1 using the humidification system 3 of the present invention will be simply described. This breathing circuit 1 is comprised of an inspiration tube 11, an exhalation tube 12, and a Y-shaped mouthpiece 13.

An artificial respirator 2 is connected to start end of the inspiration tube 11. A terminating end of the inspiration tube 11 and a starting end of the exhalation tube 12 are respectively connected to corresponding ends of the mouthpiece 13. The mouthpiece 13 is worn by a patient, enabling the patient to breath.

This type of breathing circuit 1 and artificial respirator 2 are well known in the art and so detailed description will be omitted.

A humidification system 3 of this embodiment is provided with a humidification section 31, a flow section 32, a control section 33, a reservoir 34, a pump 35, and a heating section 36 as main structural elements.

The humidification section 31 is arranged inside the inspiration tube 11 of the breathing circuit 1 (refer to FIG. 1)

The humidification section 31 of this embodiment is arranged close to a patient side end section of the inspiration tube 11. It is preferable to provide attachment fittings (not shown) for fixing respective positional relationships between the humidification section 31 and the inspiration tube 11.

The humidification section 31 is constructed able to supply moisture into intake air flowing in the inspiration tube 11. Specifically, the humidification section 31 of this embodiment is constructed using hydrophobic hollow fibers. Heated water delivered by the flow section 32 passes through the hydrophobic hollow fibers making up the humidification section 31 and it is possible for moisture to be dispersed into intake air from microscopic holes formed in side walls of the hydrophobic hollow fibers.

However, it is also possible to have a hydrophobic membrane used as part of the side wall of the flow section 32 as the humidification section 31. Basically, it is possible for the humidification section 31 to have a structure that can disperse or supply moisture supplied to the humidification section 31 into intake air.

The flow section 32 comprises a supply section 321 for supplying moisture to the humidification section 31, and a delivery section 322 for delivering moisture that has been supplied to the humidification section 31. With this embodiment, the supply section 321 and the delivery section 322 can be constructed using pliable tubes.

It is also possible to arrange all or part of the supply section 321 and the delivery section 322 inside the inspiration tube 11 (Refer to FIG. 1). The supply section 321 and the delivery section 322 have sections that pass through side walls of the inspiration tube 11 attached via appropriate seal members (not shown) to the side walls so as to maintain an airtight state of the inspiration tube 11.

A starting end of the supply section 321 is connected to the reservoir 34 via the heating section 36 and the pump 35. The terminating end of the supply section 321 is connected to the humidification section 31.

The starting end of the delivery section 322 is connected to the terminating end of the humidification section 31. The terminating end of the delivery section 322 is connected to the reservoir 34.

The control section 33 is configured to detect abnormality using difference information for water temperature of the supply section 321 and water temperature of the delivery section 322. This type of control section 33 can be simply constructed by using an appropriate control microcomputer or personal computer.

Also, as a method for detecting water temperature in the supply section 321 and the delivery section 322, it is possible to use various methods that exist in the related art. For example, it is possible to attach suitable temperature probes to the inside or side surfaces of the supply section 321 and the delivery section 322 and bring measurement values of these temperature probed into the control section 33.

The control section 33 of this embodiment is configured to detect abnormality on the condition that a difference $\Delta T$ between water temperature $T_1$ of the supply section 321 and water temperature $T_2$ of the delivery section 322 is less than or equal to a specified value $T_{th}$. If this is represented as an equation, it can be described as follows.

$$|T_1-T_2| \leq T_{th}$$

Naturally, it will be understood that $$|T_1-T_2| < T_{th}$$

and so it is possible to effectively use an equivalent conditional equation. It is also possible for the specified value $T_{th}$ to be appropriately set by an operator, depending on the purpose or situation, or to be automatically set by the control section 33 using some conditions.

The reservoir 34 is for storing water that has been pumped to the humidification section 31. Also, the reservoir 34 receives water that has been pumped to the humidification section 31 via the delivery section 322. It is possible to use anything that has heat-retaining properties as the reservoir 34.

The pump 35 pumps water stored in the reservoir 34 to the supply section 321 of the flow section 32. Pressure of the moisture delivered from the pump 35 is preferably a higher value than the internal pressure of the inspiration tube 11 of the breathing circuit 1. For example, with this embodiment, pressure of water delivered from the pump 35 is set so as to satisfy the following conditions.

$$P_1 > P_2 + P_h \geq P_{aw}$$

Here:
$P_1$: delivery pressure from pump
$P_2$: internal pressure of delivery section 322
$P_h$: pressure corresponding to height or water height h of reservoir 34
$P_{aw}$: pressure inside inspiration tube The heating section 36 heats water that has been delivered by the pump 35. This type of heating section 36 can be easily constructed using a suitable heater. The heating section 36 of this embodiment is constructed so as to heat the water that has been delivered from the pump 35 to a temperature of 60-70 degrees.

Operation of this Embodiment

Next, operation of the humidification system of this embodiment will be described. First of all, as a prerequisite, the humidification section 31 is already arranged inside the inspiration tube 11, as shown in FIG. 1. Then, water (moisture) inside the reservoir 34 is delivered to the heating section 36 by the pump 35. In this way, the water temperature is raised to a prescribed or appropriate temperature. The water temperature $T_1$ after heating is acquired by the control section 33 and stored.

Next, the warm water passes through the supply section 321 of the flow section 32 and reaches the humidification section 31. Moisture is diffused into the intake air by the humidification section 31. In this way it is possible to raise the humidity of the intake air. Also with this embodiment, since warm water is flowing in the humidification section 31, it is possible to warm the intake air.

Moisture that has passed through the humidification section 31 passes through the delivery section 322 and returns to the reservoir 34. The water temperature $T_2$ during this passage (outside the inspiration tube 11) is acquired by the control section 33 and stored.

The control section 33 determines that there is an abnormality in the intake air if the difference $\Delta T$ between the water temperature $T_1$ and the water temperature $T_2$ is less than or equal to a prescribed value, and generates an alarm.

If there is not an abnormality in intake air sent from the artificial respirator 2, the warm water flowing in the humidification section 31 and the flow section 32, and the intake air flowing in the inspiration tube 11, are subjected to heat exchange. In this way, the temperature of the moisture that has passed through the humidification section 31 is lowered. Here, if a problem arises in the artificial respirator 2 or the inspiration tube 11, for example, and the flow of intake air stops or slows down, the amount of heat exchange between the warm water and the intake air is lowered. If this is done, the difference $\Delta T$ between the water temperature $T_1$ and the water temperature $T_2$ (strictly speaking, the absolute value of that difference) is reduced.

Accordingly, using information on the water temperature difference $\Delta T$, as in this embodiment (for example, using information such as $\Delta T$ being less than or equal to a specified value), it is possible to detect intake abnormality. If it is possible to detect intake abnormality, it is possible to take appropriate action such as emitting an alarm, for example, Also, with this embodiment, at least part of the flow section 32 is arranged inside the inspiration tube, which means that it is also possible to perform warming of the intake air using warm water flowing in the flow section 32.

Also, with this embodiment, at least part of the flow section 32 is arranged inside the inspiration tube, which means that it is also possible to perform heat exchange with the intake air using warm water flowing in the flow section 32. If this is done, the amount of heat exchange between the warm water and the intake air becomes large compared to the case where heat exchange is carried out only with the humidification section 31. Therefore, with this embodiment a difference in heat exchange amount (that is, temperature difference $\Delta T$) for the case when intake air is stopped and the case where there is intake air becomes large, and there is the advantage that it is possible to raise detection sensitivity for abnormalities (SN ratio).

Conventionally, technology has been proposed to heat intake air using a heating wire but, in this case, if intake air is started again after being stopped for any reason there was a possibility of intake air that has been heated to quite a high temperature being supplied to the patient and thus distressing the patient. Conversely, according to this embodiment, since the intake air is heated using warm water, there is the advantage that the intake air temperature is never so high that it will distress the patient and usability for the patient is good.

Also, with this embodiment, the pressure of water delivered from the pump 35 is a higher value than the internal pressure of the inspiration tube 11 of the breathing circuit 1, which means that it is possible to reliably supply warm water to the humidification section 31.

Also, in a case where warm water is supplied to the humidification section 31 by negative pressure inside the humidification section 31 and, further, the humidification section 31 is permeable, there is a danger that it will not be possible to supply warm water to the humidification section 31. With this embodiment however, warm water is delivered to the humidification section 31 from the pump 35 using positive pressure, which means that there is the advantage that it is possible to reliably supply warm water to the humidification section 31.

Further, with this embodiment, since the humidification section 31 is arranged close to the patient side, temperature reduction of the intake air after humidification is slight. Accordingly, there is the advantage that according to this embodiment it is made difficult for condensation to occur inside the inspiration tube 11. In the case of a structure in which condensation arises, there is a need to provide a water removal mechanism, etc., in the breathing circuit so that water due to condensation does not reach the patient's respiratory organs. With this embodiment, since the structure is such that condensation is unlikely to arise, it is possible to simplify the structure of the breathing circuit.

Incidentally, the description of each embodiment is merely a single example and does not represent the essential structure of the present invention. The structure of each section is not limited to the above description above as long as it can realize the object of the present invention.

Further, it is also possible for the functional elements such as the above-described control section 33 to be combined and consolidated into a single functional element. It is also possible for the function of a single functional element to be realized by the cooperation of a plurality of functional elements. It is further possible for the above-described functional elements to exist as functions and as means for function implementation it is possible to use any of hardware, computer software, or a combination of the two. A single functional element can be realized by cooperation between hardware arranged at a physically separate location, and computer software.

While illustrative embodiments have been illustrated and described, it will be appreciated that various changes can be made therein without departing from the spirit and scope of the invention.

The embodiments of the invention in which an exclusive property or privilege is claimed are defined as follows:

1. A humidification system for a breathing circuit, comprising:
a humidification section, a flow section, a control section, a reservoir, and a pump, wherein
the humidification section is constructed using one of hydrophobic fiber and hydrophobic membrane wherein heated water can pass through inside one of the hydrophobic fiber and the hydrophobic membrane,
the humidification section being arranged inside an inspiration tube of the breathing system,
the humidification section being constructed to allow the heated water to pass through inside one of the hydrophobic fiber and the hydrophobic membrane to supply moisture derived from the heated water into intake air flowing inside the inspiration tube and flowing outside one of the hydrophobic fiber and the hydrophobic membrane,
the flow section comprising a supply section for supplying the heated water to the humidification section, and a delivery section for delivering the heated water that has been supplied to the humidification section to the reservoir,
the control section being configured to detect abnormality using difference information for the heated water temperature of the supply section and the heated water temperature of the delivery section, and
the pump being configured to apply pressure to the heated water for delivering the heated water to the supply section in positive pressure so that pressure of the heated water delivered to the flow section and the humidification section is higher than inner pressure in the inspiration tube of the breathing system.

2. The humidification system for a breathing circuit as disclosed in claim 1, wherein the humidification section is arranged close to a patient side end section of the inspiration tube.

3. The humidification system for a breathing circuit as disclosed in claim 1, wherein the supply section and the delivery section are constructed using flexible tube and wherein part or all of the supply section and the delivery section of the flow section is arranged inside the inspiration tube.

4. The humidification system for a breathing circuit as disclosed in claim 1, wherein the control section performs the abnormality detection on condition that a difference between the heated water temperature in the supply section and the heated water temperature in the delivery section is less than or equal to a specified value.

5. The humidification system for a breathing circuit as disclosed in claim 1, wherein the temperature of the heated water delivered to the supply section is set between about 60-70 degrees.

6. The humidification system for a breathing circuit as disclosed in claim 1, wherein the temperature of the heated water in the supply section and the heated water in the delivery section is measured outside of the inspiration tube.

7. A humidification system for a breathing circuit, comprising:
a humidification section, a flow section, a control section, a reservoir, and a pump, wherein
the humidification section being arranged inside an inspiration tube of the breathing system,
the humidification section being constructed to supply moisture derived from heated water into intake air flowing inside the inspiration tube,
the flow section comprising a supply section for supplying the heated water to the humidification section, and a delivery section for delivering the heated water that has been supplied to the humidification section to the reservoir,
the control section being configured to detect abnormality using difference information for the heated water temperature of the supply section and the heated water temperature of the delivery section, and the pump being configured to apply pressure to the heated water for delivering the heated water to the supply section in positive pressure so that pressure of the heated water delivered to the flow section and the humidification section is higher than inner pressure in the inspiration tube of the breathing system.

8. The humidification system for a breathing circuit as disclosed in claim 7, wherein the humidification section is arranged close to a patient side end section of the inspiration tube.

9. The humidification system for a breathing circuit as disclosed in claim 7, wherein the supply section and the delivery section are constructed using flexible tube and wherein part or all of the supply section and the delivery section of the flow section is arranged inside the inspiration tube.

10. The humidification system for a breathing circuit as disclosed in claim 7, wherein the control section performs the abnormality detection on condition that a difference between the heated water temperature in the supply section and the heated water temperature in the delivery section is less than or equal to a specified value.

11. The humidification system for a breathing circuit as disclosed in claim 7, wherein the temperature of the heated water delivered to the supply section is set between about 60-70 degrees.

12. The humidification system for a breathing circuit as disclosed in claim 7, wherein the temperature of the heated water in the supply section and the heated water in the delivery section is measured outside of the inspiration tube.

* * * * *